United States Patent [19]

Wilson

[11] 4,338,935
[45] Jul. 13, 1982

[54] SYRINGE SUPPORT

[76] Inventor: Elmer C. Wilson, 1951 Guy Way, Baltimore, Md. 21222

[21] Appl. No.: 221,898

[22] Filed: Dec. 31, 1980

[51] Int. Cl.³ .............................................. A61M 5/00
[52] U.S. Cl. ............................................... 128/218 R
[58] Field of Search ........... 128/213, 215, 216, 218 R, 128/218 C, 218 A, 234

[56] References Cited

U.S. PATENT DOCUMENTS 2,491,978  12/1949  Helfman .......................... 128/218 R
4,022,207  5/1977   Citrin ............................... 128/218 C Primary Examiner—John D. Yasko Attorney, Agent, or Firm—Shlesinger, Arkwright, Garvey & Dinsmore

[57] ABSTRACT

A syringe support having a horizontal body portion, a first bracket member for holding a syringe plunger head in position and a second bracket member for slideably holding a syringe barrel while the support is clamped to a table. A patient may self-administer a medicinal dose contained in the syringe by placing a loaded syringe in the support and pressing his arm or other body portion against the needle of the syringe. Continued pressure against the needle causes injection by forcing the syringe barrel to slide along the support horizontal body portion in relation to the fixed piston or plunger until the cylinder abuts the second bracket member.

12 Claims, 5 Drawing Figures

U.S. Patent  Jul. 13, 1982  4,338,935
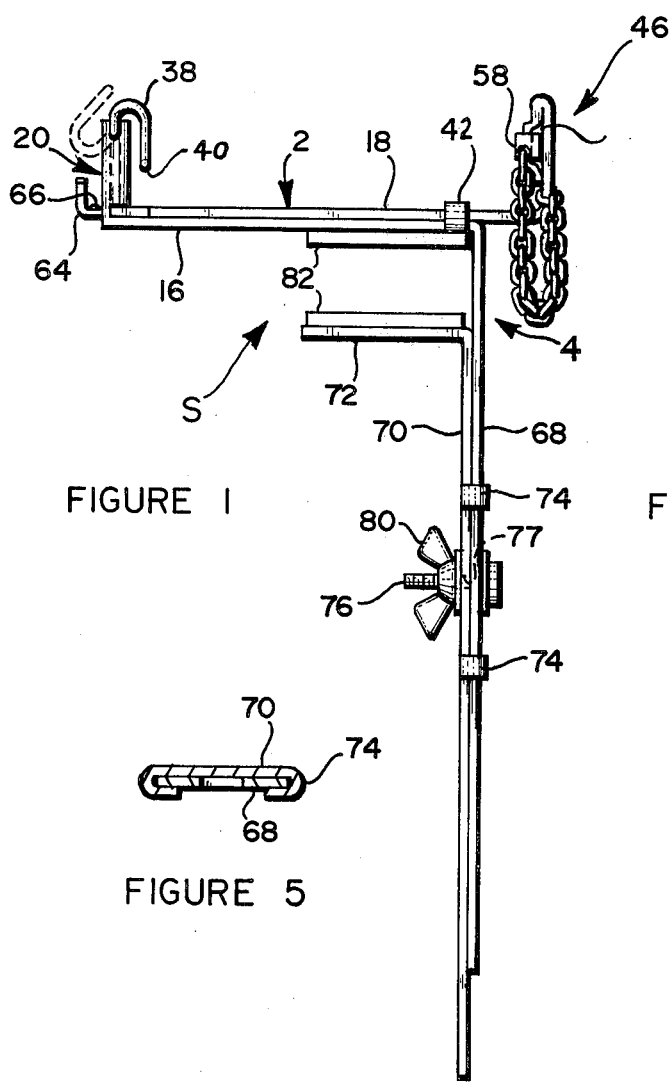
FIGURE 1
FIGURE 5
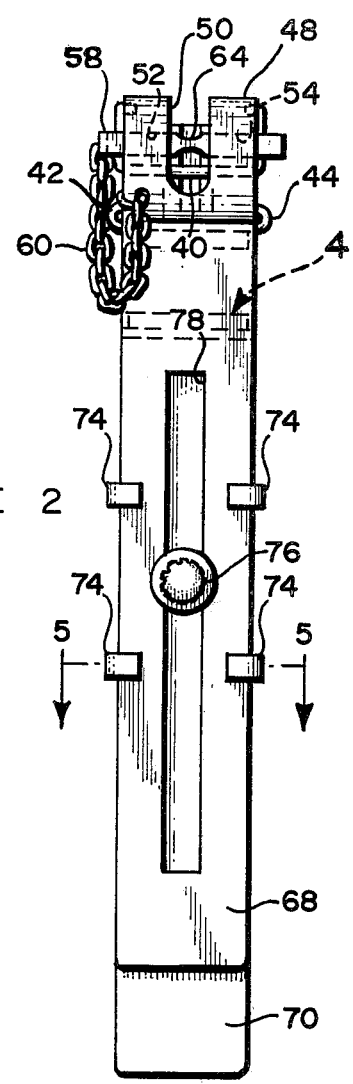
FIGURE 2
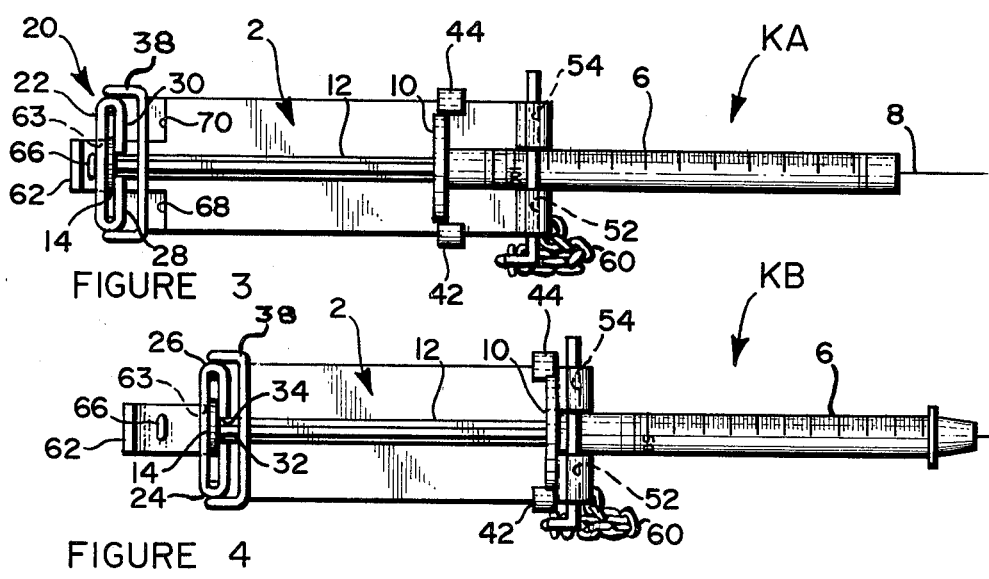
FIGURE 3
FIGURE 4

SYRINGE SUPPORT

BACKGROUND AND FIELD OF THE INVENTION

This invention relates to syringe supports for securing a syringe to a table or the like. In particular, the present invention relates to syringe supports for securing a syringe in position to enable patients, such as diabetics, to self-administer predetermined doses of medicine.

Generally, syringe supports have been used in hospitals or the like for securing a syringe in position while a machine plunger arm or similar apparatus either extracts or expels a sample from the syringe. Typical of such supports are those disclosed in U.S. Pat. Nos. 2,463,400 to Lowe, 3,833,030 to Waldbauer 3,875,979 to Hults and 3,841,331 to Wilder. None of the prior art inventions, however, provide a springe support which sufficiently enables a patient to easily and efficiently self-administer a medicinal dose. Presently, many diabetics who require daily injections of insulin, use a standard syringe and, by hand, self-administer a dose of insulin. This procedure however, is sometimes awkward and difficult especially for persons with reduced coordination and hand dexterity such as the elderly. Also with older people, the skin loses its firmness and a portion must be pinched by one hand making injection impossible without the assistance of a second party.

OBJECTS AND SUMMARY OF THE INVENTION

It is therefore one object of the present invention to provide a syringe support which when clamped to a table will enable a patient with reduced coordination, or an elderly person with loose tissue, to self-administer a medicinal dose without the need for a second party.

It is another object of the present invention to provide a syringe support which holds a plunger head stationary while a patient applies pressure against the needle causing the syringe barrel to slide towards the plunger head and administer a medicinal dose.

It is a further object of the present invention to provide a syringe support which has a horizontal body portion which is extensible to adapt the support for various size syringes.

It is a still further object of the present invention to provide a syringe support having a horizontal body section which is selectively positionable to predetermined positions for administering selected doses from various sizes of syringes.

It is another object of the present invention to provide a syringe support which will prevent lateral or vertical movement of a syringe during injection and administration of the medicine to thereby reduce discomfort to the administrator.

A further object of this invention is to provide a support for a medicinal syringe which can be clamped to different sizes and articles of furniture or the like of different thickness and dimensions.

These and other objects of the present invention are accomplished by a syringe support having a horizontal body portion, a first bracket member for holding a syringe barrel while the entire syringe support is securely clamped to a table or other stationary object which will be further apparent from the following description and claims.

DESCRIPTION OF THE DRAWINGS

In the accompanying drawings which illustrate by way of example various embodiments of this invention:

FIG. 1 is a side elevational view of the syringe support of the present invention.

FIG. 2 is a front elevational view of the syringe support of the present invention.

FIG. 3 is a top plan view of the syringe support of the present invention with one type of a syringe held within the support.

FIG. 4 is a top plan view of the present invention with another type syringe held within the support.

FIGURE is a cross section view taken along the lines 5—5 of FIG. 2 and seen in the direction of the arrows.

DETAILED DESCRIPTION OF THE INVENTION

Referring now to the various figures, the syringe support S is generally comprised of a horizontal body portion 2 and a clamp section 4 attached thereto and can be constructed of stock metal, plastic or other materials which will provide a support sufficiently sturdy to adequately secure a syringe. The syringe support S is adapted to hold typical syringes such as KA and KB in FIGS. 3 and 4 having a barrel 6 with a needle 8 at one end, a flange 10 at the other end and a plunger 12 slideable within a barrel and having a plunger head 14 at the end thereof.

The means for holding a syringe on the support is provided for on the horizontal body portion 2 which consists of a lower horizontal portion 16 and an upper horizontal portion 18 which is slideable with respect to a lower horizontal portion 16. Lower horizontal portion 16 at its one end is continuous with clamp 4 as described hereinafter and at its other end is continuous with bracket 20 which extends substantially perpendicularly upward from lower horizontal portion 16 and provides the means for securing plunger head 14. Bracket 20 includes back wall 22 and curve sides 24 and 26 which continue to front wall portions 28 and 30 whose ends 32 and 34 are spaced apart forming a slot for receiving plunger 12 while plunger head 14 is held within the walls of bracket 20. So as to prevent plunger 12 and plunger head 14 from inadvertently becoming disengaged with bracket 20, latch 38 is pivotally attached to side walls 24 and 26 of bracket 20 and includes horizontal bar 40 for urging against plunger 12 as shown to advantage in FIGS. 3 and 4. To allow for placement and removal of a syringe plunger 12, latch 38 can be moved from its closed position as shown in FIGS. 3 and 4 to its open position as shown by the dotted lines in FIG. 1.

In order to make the syringe support S adaptable to various size syringes, upper horizontal portion 18 is made to be slidably movable with respect to lower portion 16 within restraining flanges 42 and 44 extending from the lower horizontal portion 16 to prevent upper horizontal portion 18 from inadvertently moving vertically with respect to the rest of the syringe support S. Upper horizontal portion 18 at its one end is continuous with bracket 46 which extends substantially vertically from upper horizontal portion 18 and consists of a bracket plate 48 having a slot 50 cut therein for receiving a syringe barrel 6. Bracket 46 also includes key holders 52 and 54 containing key holes 56 in which can be inserted securing key 58. Securing key 58 is attached to bracket 46 by a chain 60 or similar attaching means and is inserted into key hole 56 to prevent a barrel 6 from inadvertently moving vertically within slot 50. As shown to advantage by FIGS. 1 and 2, securing key 58 may be generally flat or cylindrical or other configurations and made of metal, plastic or other materials with opposing depressions 64 in the outer surfaces thereof which will conform to the generally cylindrical contour of a syringe barrel 6 so as to not interfere with the sliding movement of a barrel 6 while key 58 extends across slot 50 preventing vertical movement of the barrel 6.

As previously stated, the horizontal body portion 2 of the syringe support S of the present invention is extensible and selectively positionable to permit the support S to properly receive various size of syringes such as KA and KB. This selected positioning of upper horizontal portion 18 is made possible by providing an extension tongue 62 at the end of upper horizontal portion 18 distant from bracket 46. Extension tongue 62 extends through a slot 63 (shown in dotted lines in FIGS. 3 and 4) in bracket 20, terminates at vertical tongue portion 64 and is provided with a small stop protrusion 66. To selectively extend the support S to receive a 100 cc syringe KA, as shown to advantage in FIGS. 1 and 3, upper horizontal portion 18 is slideably extended moving bracket 46 away from bracket 20 until stop protrusion 66 abuts back wall 22 of the bracket 20. Syringe support S is then properly extended to receive a 100 cc syringe KA. To adapt the syringe support S to receive a 50 cc syringe KB as in FIG. 4, upper horizontal portion 18 is slideably moved bringing bracket 46 closer to bracket 20 until end edges 68 and 70 of upper horizontal portion 18 abut front walls 28 and 30 of bracket 20, respectively. The syringe support S is thus easily and quickly adapted to support either a 50 cc KB or 100 cc KA syringe, by selectively sliding upper horizontal portion 18 to predetermined points with respect to lower horizontal portion 16.

When the syringe support S is to be used by a patient for self-administering medicinal doses, it will ordinarily be clamped to a table or other secured horizontal surface and therefore, syringe support S is provided with clamp 4 for properly securing the support while in use. Clamp 4 includes an outer standard 68 which is continuous with and extends substantially perpendicular from lower horizontal portion 16. Slideably associated with outer standard 68 is inner standard 70 which continues at its end closest to body portion 2 to horizontal clamp portion 72. Inner standard 70 includes four holddown flanges 74 which partially wrap around outer standard 68 to prevent the inner and outer standard from becoming separated from one another. To further prevent the inner and outer standards from becoming separated and to tighten the clamp portion 72 about a table, a bolt 76 is provided extending through a hole 77 in inner standard 70, slideable within guideway 78 of outer standard 68 and tightened with wingnut 80. The clamp 4 is further provided with rubber or similar resilient pads 82 to prevent the clamp from scratching or marring a table or other object to which the support is attached.

In its proper operation, the syringe support S is first securely attached to a table by placing the rubber pads 82 around the table outer edge and tightening the clamp 4 so that horizontal body portion 2 is substantially perpendicular to the table outer edge with bracket 46 slightly extending over the table. The syringe support is then set for receiving either a 50 cc KB or 100 cc KA syringe by properly positioning upper horizontal portion 18 with respect to lower horizontal portion 16. If a 100 cc syringe KA is to be used, upper horizontal portion 16 will be extended so that stop protrusion 66 abuts back wall 22 of bracket 20 and, alternatively, if a 50 cc syringe KB is to be used, upper horizontal portions 18 will be extended so that ends 68 and 70 abut front walls 28 and 30 of bracket 20. Once the horizontal body portion 2 has been properly positioned, latch 38 is moved to its open position and a syringe is placed within support S with a barrel 6 contained within slot 50, a plunger 12 positioned within the slot of bracket 20 and a plunger head 14 positioned within bracket 20. The syringe is then secured within the support by pivoting latch 38 to its closed position and inserting key 58 within keyholes 56 of key holders 52 and 54, as shown to advantage in FIGS. 3 and 4. A dibbetic or other patient will then self-administer a medicinal dose contained within the syringe by moving his arm (or other proper portion of the body) against needle 18 and causing the needle 8 to penetrate into the skin. Continuous pressure with his arm causes the needle to penetrate to the point where barrel 6 slides within slot 50 towards bracket 20 thereby causing barrel 6 to move with respect to plunger 12 to expel the medicine contained therein. The patient will continue applying pressure against needle 8 until flange 10 of the syringe abuts front walls 28 and 30 of bracket 20 at which time the proper dose has been administered and the needle may be removed from the patient's arm.

While this invention has been described as having a preferred design, it will be understood that it is capable of further modification. This application is, therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What is claimed is:

1. In a syringe support for clamping to a table top or the like a syringe having a plunger, a barrel slideable on said plunger, and said plunger having a plunger head, that invention which includes:
   (a) a horizontal body for supporting such syringe including a longitudinal axis
   (b) a first upright bracket member on one end of said body
   (c) means for locking said plunger head in said first bracket against longitudinal axial movement relative to said body
   (d) a second upright bracket member on the other end of said body
   (e) mounting means on said second bracket member for supporting said barrel for longitudinal slideable axial movement relative to said body, and
   (f) latch means on said first bracket for preventing upward displacement of said syringe when positioned in said first and second brackets.

2. A syringe support as in claim 1, and wherein:
   (a) said horizontal body portion has extendable means for extending said body for various sized syringes.

3. A syringe support as in claim 2 and wherein:
   (a) said extendable means has upper and lower portions slideable axially with respect to each other for receiving various sizes of syringes.

4. A syringe support as in claim 3 and wherein:
   (a) said lower portion includes restraining flanges partially wrapped around said upper portion whereby said body portions are held together in a sliding relationship.

5. A syringe support as in claim 1 and wherein:
(a) said second upright bracket member includes a barrel slot and means removably positioned across said barrel slot to prevent vertical movement of said barrel with respect to said support.

6. A syringe support as in claim 1 and wherein:
(a) said locking means for plunger head includes a latch.

7. A syringe support as in claim 3 and wherein:
(a) said lower horizontal body portion includes a generally downwardly projecting mounting support, and
(b) said mounting support including a generally L-shaped clamp member slideably secured to said mounting support clamping said syringe support to a table top.

8. A syringe support as in claim 7 and wherein:
(a) said first upright bracket member, said lower body portion and said downwardly projecting support forming a continuous element.

9. A syringe support as in claim 7 and wherein:
(a) said second upright bracket member is integral with said upper portion of said extendable means and is movable with respect to said first upright bracket member.

10. A syringe support as in claim 9 and wherein:
(a) said first upright bracket member includes a first slot therein, and
(b) said upper portion of said extendable means includes a tongue extending through said first slot and slideable therein.

11. A syringe support as in claim 10 and wherein:
(a) said tongue includes a stop member for preventing disengagement of said lower portion.

12. A syringe support as in claim 1 and wherein:
(a) means for locking said plunger head against longitudinal movement includes a second slot for receiving said plunger head, and
(b) said latch means being mounted for pivotal movement about said first bracket member.

* * * * *